United States Patent
Kriksunov

(10) Patent No.: US 7,347,851 B1
(45) Date of Patent: Mar. 25, 2008

(54) NEEDLELESS HYPODERMIC JET INJECTOR APPARATUS AND METHOD

(76) Inventor: Leo B Kriksunov, 5 Perry La., Ithaca, NY (US) 14850

( * ) Notice: Subject to any disclaimer, the term of this patent is extended or adjusted under 35 U.S.C. 154(b) by 185 days.

(21) Appl. No.: 10/796,468

(22) Filed: Mar. 9, 2004

(51) Int. Cl.
*A61M 31/00* (2006.01)

(52) U.S. Cl. .......................... 604/500; 604/68; 604/70; 604/136

(58) Field of Classification Search ................. 604/68, 604/69, 70, 20, 152, 46; 422/44; 210/746, 210/739
See application file for complete search history.

(56) References Cited

U.S. PATENT DOCUMENTS

| | | |
|---|---|---|
| 146,886 A | 1/1874 | Doane et al. |
| 162,814 A | 5/1875 | Graves et al. |
| 261,090 A | 7/1882 | Grill |
| 264,412 A | 9/1882 | Kuhlmann |
| 299,480 A | 5/1884 | Kuhlmann et al. |
| 302,041 A | 7/1884 | Sill |
| 307,112 A | 10/1884 | Groff |
| 509,253 A | 11/1893 | Shields |
| 545,504 A | 9/1895 | Hoover |
| 869,513 A | 10/1907 | Pfell |
| 941,726 A | 11/1909 | Pfalzgraf |
| 997,720 A | 7/1911 | Troupenat |
| 1,037,843 A | 9/1912 | Ackley |
| 1,050,649 A | 1/1913 | Harrold et al. |
| 1,054,558 A | 2/1913 | Jones |
| 1,074,198 A | 9/1913 | Phillips |
| 1,082,870 A | 12/1913 | Humason |
| 1,101,515 A | 6/1914 | Adam |
| 1,126,970 A | 2/1915 | Folmer |
| 1,132,129 A | 3/1915 | Stevens |
| 1,148,169 A | 7/1915 | Howe |
| 1,154,209 A | 9/1915 | Rushton |
| 1,205,246 A | 11/1916 | Mowry |
| 1,228,047 A | 5/1917 | Reinhold |
| 1,240,430 A | 9/1917 | Erickson |
| 1,244,187 A | 10/1917 | Frisbie |
| 1,255,886 A | 2/1918 | Jones |
| 1,258,961 A | 3/1918 | Tattersall |
| 1,311,508 A | 7/1919 | Harrold |
| 1,324,136 A | 12/1919 | Turner |
| 1,381,612 A | 6/1921 | Anderson |
| 1,397,606 A | 11/1921 | Smith |
| 1,427,005 A | 8/1922 | McMichael |
| 1,430,983 A | 10/1922 | Granberg |
| 1,464,924 A | 8/1923 | Drummond |
| 1,465,224 A | 8/1923 | Lantz |
| 1,496,212 A | 6/1924 | French |

(Continued)

FOREIGN PATENT DOCUMENTS

WO    WO 97/37705    10/1997

*Primary Examiner*—Kevin C. Sirmons
*Assistant Examiner*—Phillip Gray
(74) *Attorney, Agent, or Firm*—Leo B. Kriksunov

(57) ABSTRACT

In the present invention, the impedance between patient's body and the jet injection drug delivery device is measured through the liquid jet during the drug delivery process. The liquid jet completes the electrical circuit formed by impedance monitor, drug delivery device, and the patient's body. When the jet pierces stratum corneum, the impedance in the circuit immediately decreases, thus an indicating the successful drug delivery. The impedance monitor then provides a signal, visible, audible, or electronic, indicating that the process of the drug delivery through skin was successful.

9 Claims, 3 Drawing Sheets

U.S. PATENT DOCUMENTS

| | | |
|---|---|---|
| 1,511,797 A | 10/1924 | Berghold |
| 1,526,128 A | 2/1925 | Flohr |
| 1,527,587 A | 2/1925 | Hutchinson |
| 1,551,900 A | 9/1925 | Morrow |
| 1,553,996 A | 9/1925 | Federer |
| 1,600,604 A | 9/1926 | Sorlien |
| 1,616,478 A | 2/1927 | Watson |
| 1,640,517 A | 8/1927 | Procknow |
| 1,662,372 A | 3/1928 | Ward |
| 1,701,948 A | 2/1929 | Crowe |
| 1,711,490 A | 5/1929 | Drummond |
| 1,712,828 A | 5/1929 | Klehm |
| 1,774,521 A | 9/1930 | Neighbour |
| 1,807,120 A | 5/1931 | Lewis |
| 1,811,066 A | 6/1931 | Tannewitz |
| 1,879,280 A | 9/1932 | James |
| 1,896,924 A | 2/1933 | Ulrich |
| 1,902,270 A | 3/1933 | Tate |
| 1,904,005 A | 4/1933 | Masset |
| 1,910,651 A | 5/1933 | Tautz |
| 1,938,548 A | 12/1933 | Tautz |
| 1,938,549 A | 12/1933 | Tautz |
| 1,963,688 A | 6/1934 | Tautz |
| 1,988,102 A | 1/1935 | Woodward |
| 1,993,219 A | 3/1935 | Merrigan |
| 2,007,887 A | 7/1935 | Tautz |
| 2,010,851 A | 8/1935 | Drummond |
| 2,020,222 A | 11/1935 | Tautz |
| 2,038,810 A | 4/1936 | Tautz |
| 2,075,282 A | 3/1937 | Hedgpeth |
| 2,095,330 A | 10/1937 | Hedgpeth |
| 2,106,288 A | 1/1938 | Tautz |
| 2,108,321 A | 1/1938 | Guertin |
| 2,121,069 A | 6/1938 | Collins |
| 2,131,492 A | 9/1938 | Ocenasek |
| 2,163,320 A | 6/1939 | Hammond |
| 2,168,282 A | 8/1939 | Tautz |
| 2,241,556 A | 5/1941 | MacMillin et al. |
| 2,261,696 A | 11/1941 | Ocenasek |
| 2,265,407 A | 12/1941 | Tautz |
| 2,286,589 A | 6/1942 | Tannewitz |
| 2,292,872 A | 8/1942 | Eastman |
| 2,299,262 A | 10/1942 | Uremovich |
| 2,312,118 A | 2/1943 | Neisewander |
| 2,313,686 A | 3/1943 | Uremovich |
| 2,328,244 A | 8/1943 | Woodward |
| 2,352,235 A | 6/1944 | Tautz |
| 2,377,265 A | 3/1945 | Rady |
| 2,425,331 A | 8/1947 | Kramer |
| 2,434,174 A | 1/1948 | Morgan |
| 2,466,325 A | 4/1949 | Ocenasek |
| 2,496,613 A | 2/1950 | Woodward |
| 2,509,813 A | 5/1950 | Dineen |
| 2,517,649 A | 8/1950 | Frechtmann |
| 2,518,684 A | 8/1950 | Harris |
| 2,530,290 A | 11/1950 | Collins |
| 2,554,124 A | 5/1951 | Salmont |
| 2,572,326 A | 10/1951 | Evans |
| 2,590,035 A | 3/1952 | Pollak |
| 2,593,596 A | 4/1952 | Olson |
| 2,623,555 A | 12/1952 | Eschenburg |
| 2,625,966 A | 1/1953 | Copp |
| 2,626,639 A | 1/1953 | Hess |
| 2,661,777 A | 12/1953 | Hitchcock |
| 2,661,780 A | 12/1953 | Morgan |
| 2,675,707 A | 4/1954 | Brown |
| 2,678,071 A | 5/1954 | Odlum et al. |
| 2,690,084 A | 9/1954 | Van Dam |
| 2,695,638 A | 11/1954 | Gaskell |
| 2,704,560 A | 3/1955 | Woessner |
| 2,711,762 A | 6/1955 | Gaskell |
| 2,722,246 A | 11/1955 | Arnoldy |
| 2,731,049 A | 1/1956 | Akin |
| 2,736,348 A | 2/1956 | Nelson |
| 2,758,615 A | 8/1956 | Mastriforte |
| 2,785,710 A | 3/1957 | Mowery, Jr. |
| 2,786,498 A | 3/1957 | Eschenburg |
| 2,810,408 A | 10/1957 | Boice et al. |
| 2,844,173 A | 7/1958 | Gaskell |
| 2,850,054 A | 9/1958 | Eschenburg |
| 2,852,047 A | 9/1958 | Odlum et al. |
| 2,873,773 A | 2/1959 | Gaskell |
| 2,894,546 A | 7/1959 | Eschenburg |
| 2,913,025 A | 11/1959 | Richards |
| 2,945,516 A | 7/1960 | Edgemond, Jr. et al. |
| 2,954,118 A | 9/1960 | Anderson |
| 2,978,084 A | 4/1961 | Vilkaitis |
| 2,984,268 A | 5/1961 | Vuichard |
| 3,005,477 A | 10/1961 | Sherwen |
| 3,011,529 A | 12/1961 | Copp |
| 3,011,610 A | 12/1961 | Stiebel et al. |
| 3,013,592 A | 12/1961 | Ambrosio et al. |
| 3,021,881 A | 2/1962 | Edgemond, Jr. et al. |
| 3,047,116 A | 7/1962 | Stiebel et al. |
| 3,085,602 A | 4/1963 | Gaskell |
| 3,105,530 A | 10/1963 | Peterson |
| 3,129,731 A | 4/1964 | Tyrrell |
| 3,163,732 A | 12/1964 | Abbott |
| 3,186,256 A | 6/1965 | Reznick |
| 3,207,273 A | 9/1965 | Jurin |
| 3,224,474 A | 12/1965 | Bloom |
| 3,232,326 A | 2/1966 | Speer et al. |
| 3,249,134 A | 5/1966 | Vogl et al. |
| 3,306,149 A | 2/1967 | John |
| 3,315,715 A | 4/1967 | Mytinger |
| 3,323,814 A | 6/1967 | Phillips |
| 3,356,111 A | 12/1967 | Mitchell |
| 3,386,322 A | 6/1968 | Stone et al. |
| 3,454,286 A | 7/1969 | Anderson et al. |
| 3,538,964 A | 11/1970 | Warrick et al. |
| 3,540,338 A | 11/1970 | McEwan et al. |
| 3,554,067 A | 1/1971 | Scutella |
| 3,581,784 A | 6/1971 | Warrick |
| 3,613,748 A | 10/1971 | De Pue |
| 3,670,788 A | 6/1972 | Pollak et al. |
| 3,675,444 A | 7/1972 | Whipple |
| 3,680,609 A | 8/1972 | Menge |
| 3,695,116 A | 10/1972 | Baur |
| 3,745,546 A | 7/1973 | Struger et al. |
| 3,749,933 A | 7/1973 | Davidson |
| 3,754,493 A | 8/1973 | Niehaus et al. |
| 3,772,590 A | 11/1973 | Mikulecky et al. |
| 3,785,230 A | 1/1974 | Lokey |
| 3,805,639 A | 4/1974 | Peter |
| 3,805,658 A | 4/1974 | Scott et al. |
| 3,808,932 A | 5/1974 | Russell |
| 3,829,850 A | 8/1974 | Guetersloh |
| 3,858,095 A | 12/1974 | Friemann et al. |
| 3,861,016 A | 1/1975 | Johnson et al. |
| 3,880,032 A | 4/1975 | Green |
| 3,889,567 A | 6/1975 | Sato et al. |
| 3,922,785 A | 12/1975 | Fushiya |
| 3,924,688 A | 12/1975 | Cooper et al. |
| 3,931,727 A | 1/1976 | Luenser |
| 3,946,631 A | 3/1976 | Malm |
| 3,947,734 A | 3/1976 | Fyler |
| 3,949,636 A | 4/1976 | Ball et al. |
| 3,953,770 A | 4/1976 | Hayashi |
| 3,967,161 A | 6/1976 | Lichtblau |
| 4,007,679 A | 2/1977 | Edwards |
| 4,026,174 A | 5/1977 | Fierro |
| 4,026,177 A | 5/1977 | Lokey |
| 4,047,156 A | 9/1977 | Atkins |
| 4,048,886 A | 9/1977 | Zettler |

| | | | | | | |
|---|---|---|---|---|---|---|
| 4,060,160 A | 11/1977 | Lieber | | 5,218,189 A | 6/1993 | Hutchison |
| 4,070,940 A | 1/1978 | McDaniel et al. | | 5,231,906 A | 8/1993 | Kogej |
| 4,075,961 A | 2/1978 | Harris | | 5,245,879 A | 9/1993 | McKeon |
| 4,077,161 A | 3/1978 | Wyle et al. | | 5,257,570 A | 11/1993 | Shiotani et al. |
| 4,085,303 A | 4/1978 | McIntyre et al. | | 5,265,510 A | 11/1993 | Hoyer-Ellefsen |
| 4,090,345 A | 5/1978 | Harkness | | 5,272,946 A | 12/1993 | McCullough et al. |
| 4,091,698 A | 5/1978 | Obear et al. | | 5,276,431 A | 1/1994 | Piccoli et al. |
| 4,117,752 A | 10/1978 | Yoneda | | 5,285,708 A | 2/1994 | Bosten et al. |
| 4,145,940 A | 3/1979 | Woloveke et al. | | 5,320,382 A | 6/1994 | Goldstein et al. |
| 4,152,833 A | 5/1979 | Phillips | | 5,321,230 A | 6/1994 | Shanklin et al. |
| 4,161,649 A | 7/1979 | Klos et al. | | 5,331,875 A | 7/1994 | Mayfield |
| 4,175,452 A | 11/1979 | Idel | | 5,377,554 A | 1/1995 | Reulein et al. |
| 4,190,000 A | 2/1980 | Shaull et al. | | 5,377,571 A | 1/1995 | Josephs |
| 4,195,722 A | 4/1980 | Anderson et al. | | 5,392,678 A | 2/1995 | Sasaki et al. |
| 4,249,117 A | 2/1981 | Leukhardt et al. | | 5,471,888 A | 12/1995 | McCormick |
| 4,249,442 A | 2/1981 | Fittery | | 5,510,685 A | 4/1996 | Grasselli |
| 4,267,914 A | 5/1981 | Saar | | 5,513,548 A | 5/1996 | Garuglieri |
| 4,270,427 A | 6/1981 | Colberg et al. | | 5,534,836 A | 7/1996 | Schenkel et al. |
| 4,276,799 A | 7/1981 | Muehling | | 5,572,916 A | 11/1996 | Takano |
| 4,305,442 A | 12/1981 | Currie | | 5,587,618 A | 12/1996 | Hathaway |
| 4,321,841 A | 3/1982 | Felix | | 5,606,889 A | 3/1997 | Bielinski et al. |
| 4,372,202 A | 2/1983 | Cameron | | 5,667,152 A | 9/1997 | Mooring |
| 4,391,358 A | 7/1983 | Haeger | | 5,671,633 A | 9/1997 | Wagner |
| 4,418,597 A | 12/1983 | Krusemark et al. | | 5,695,306 A | 12/1997 | Nygren, Jr. |
| 4,466,233 A | 8/1984 | Thesman | | 5,724,875 A | 3/1998 | Meredith et al. |
| 4,470,046 A | 9/1984 | Betsill | | 5,730,165 A | 3/1998 | Philipp |
| 4,510,489 A | 4/1985 | Anderson, III et al. | | 5,730,723 A | 3/1998 | Castellano et al. |
| 4,512,224 A | 4/1985 | Terauchi | | 5,755,148 A | 5/1998 | Stumpf et al. |
| 4,518,043 A | 5/1985 | Anderson et al. | | 5,771,742 A | 6/1998 | Bokaie et al. |
| 4,532,501 A | 7/1985 | Hoffman | | 5,782,001 A | 7/1998 | Gray |
| 4,532,844 A | 8/1985 | Chang et al. | | 5,787,779 A | 8/1998 | Garuglieri |
| 4,557,168 A | 12/1985 | Tokiwa | | 5,791,057 A | 8/1998 | Nakamura et al. |
| 4,560,033 A | 12/1985 | DeWoody et al. | | 5,791,223 A | 8/1998 | Lanzer |
| 4,566,512 A | 1/1986 | Wilson | | 5,791,224 A | 8/1998 | Suzuki et al. |
| 4,573,556 A | 3/1986 | Andreasson | | 5,861,809 A | 1/1999 | Eckstein et al. |
| 4,576,073 A | 3/1986 | Stinson | | 5,875,698 A | 3/1999 | Ceroll et al. |
| 4,589,047 A | 5/1986 | Gaus et al. | | 5,921,367 A | 7/1999 | Kashioka et al. |
| 4,596,556 A | 6/1986 | Morrow et al. | | 5,937,720 A | 8/1999 | Itzov |
| 4,599,597 A | 7/1986 | Rotbart | | 5,942,975 A | 8/1999 | Sorensen |
| 4,599,927 A | 7/1986 | Eccardt et al. | | 5,943,932 A | 8/1999 | Sberveglieri |
| 4,606,251 A | 8/1986 | Boileau | | 5,950,514 A | 9/1999 | Benedict et al. |
| 4,615,247 A | 10/1986 | Berkeley | | 5,963,173 A | 10/1999 | Lian et al. |
| 4,621,300 A | 11/1986 | Summerer | | 5,989,116 A | 11/1999 | Johnson et al. |
| 4,625,604 A | 12/1986 | Handler et al. | | 6,018,284 A | 1/2000 | Rival et al. |
| 4,637,188 A | 1/1987 | Crothers | | 6,037,729 A | 3/2000 | Woods et al. |
| 4,637,289 A | 1/1987 | Ramsden | | 6,095,092 A | 8/2000 | Chou |
| 4,644,832 A | 2/1987 | Smith | | 6,119,984 A | 9/2000 | Devine |
| 4,653,189 A | 3/1987 | Andreasson | | 6,133,818 A | 10/2000 | Hsieh et al. |
| 4,722,021 A | 1/1988 | Hornung et al. | | 6,148,504 A | 11/2000 | Schmidt et al. |
| 4,751,603 A | 6/1988 | Kwan | | 6,170,370 B1 | 1/2001 | Sommerville |
| 4,757,881 A | 7/1988 | Jonsson et al. | | 6,244,149 B1 | 6/2001 | Ceroll et al. |
| 4,792,965 A | 12/1988 | Morgan | | 6,257,061 B1 | 7/2001 | Nonoyama et al. |
| 4,805,504 A | 2/1989 | Fushiya et al. | | 6,366,099 B1 | 4/2002 | Reddi |
| 4,840,135 A | 6/1989 | Yamauchi | | 6,404,098 B1 | 6/2002 | Kayama et al. |
| 4,864,455 A | 9/1989 | Shimomura et al. | | 6,405,624 B2 | 6/2002 | Sutton |
| 4,875,398 A | 10/1989 | Taylor et al. | | 6,418,829 B1 | 7/2002 | Pilchowski |
| 4,906,962 A | 3/1990 | Duimstra | | 6,420,814 B1 | 7/2002 | Bobbio |
| 4,913,699 A | 4/1990 | Parsons | | 6,430,007 B1 | 8/2002 | Jabbari |
| 4,965,909 A | 10/1990 | McCullough et al. | | 6,450,077 B1 | 9/2002 | Ceroll et al. |
| 5,025,175 A | 6/1991 | Dubois, III | | 6,453,786 B1 | 9/2002 | Ceroll et al. |
| 5,046,426 A | 9/1991 | Julien et al. | | 6,460,442 B2 | 10/2002 | Talesky et al. |
| 5,052,255 A | 10/1991 | Gaines | | 6,479,958 B1 | 11/2002 | Thompson et al. |
| 5,081,406 A | 1/1992 | Hughes et al. | | D466,913 S | 12/2002 | Ceroll et al. |
| 5,082,316 A | 1/1992 | Wardlaw | | D469,354 S | 1/2003 | Curtsinger |
| 5,086,890 A | 2/1992 | Turczyn et al. | | 6,502,493 B1 | 1/2003 | Eccardt et al. |
| 5,119,555 A | 6/1992 | Johnson | | 6,536,536 B1 | 3/2003 | Gass et al. |
| 5,122,091 A | 6/1992 | Townsend | | 6,543,324 B2 | 4/2003 | Dils |
| 5,174,349 A | 12/1992 | Svetlik et al. | | 6,546,835 B2 | 4/2003 | Wang |
| 5,184,534 A | 2/1993 | Lee | | 6,575,067 B2 | 6/2003 | Parks et al. |
| 5,198,702 A | 3/1993 | McCullough et al. | | 6,578,460 B2 | 6/2003 | Sartori |
| 5,201,684 A | 4/1993 | DeBois, III | | 6,578,856 B2 | 6/2003 | Kahle |
| 5,207,253 A | 5/1993 | Hoshino et al. | | 6,585,685 B2 * | 7/2003 | Staylor et al. ............... 604/68 |
| 5,212,621 A | 5/1993 | Panter | | 6,595,096 B2 | 7/2003 | Ceroll et al. |

| | | | | | |
|---|---|---|---|---|---|
| D478,917 S | 8/2003 | Ceroll et al. | 2002/0066346 A1 | 6/2002 | Gass et al. |
| 6,601,493 B1 | 8/2003 | Crofutt | 2002/0069734 A1 | 6/2002 | Gass et al. |
| 6,607,015 B1 | 8/2003 | Chen | 2002/0096030 A1 | 7/2002 | Wang |
| D479,538 S | 9/2003 | Welsh et al. | 2002/0109036 A1 | 8/2002 | Denen et al. |
| 6,619,348 B2 | 9/2003 | Wang | 2002/0170399 A1 | 11/2002 | Gass et al. |
| 6,640,683 B2 | 11/2003 | Lee | 2002/0170400 A1 | 11/2002 | Gass |
| 6,644,157 B2 | 11/2003 | Huang | 2002/0190581 A1 | 12/2002 | Gass et al. |
| 6,647,847 B2 | 11/2003 | Hewitt et al. | 2003/0002942 A1 | 1/2003 | Gass et al. |
| 6,689,093 B2 | 2/2004 | Landau | 2003/0005588 A1 | 1/2003 | Gass et al. |
| 7,138,088 B2 * | 11/2006 | Wariar et al. ................. 422/44 | 2003/0015253 A1 | 1/2003 | Gass et al. |
| 2002/0017181 A1 | 2/2002 | Gass et al. | 2003/0019341 A1 | 1/2003 | Gass et al. |
| 2002/0017182 A1 | 2/2002 | Gass et al. | 2003/0020336 A1 | 1/2003 | Gass et al. |
| 2002/0017183 A1 | 2/2002 | Gass et al. | 2003/0037651 A1 | 2/2003 | Gass et al. |
| 2002/0017184 A1 | 2/2002 | Gass et al. | 2003/0056853 A1 | 3/2003 | Gass et al. |
| 2002/0017336 A1 | 2/2002 | Gass et al. | 2003/0058121 A1 | 3/2003 | Gass et al. |
| 2002/0020261 A1 | 2/2002 | Gass et al. | 2003/0074873 A1 | 4/2003 | Freiberg et al. |
| 2002/0020262 A1 | 2/2002 | Gass et al. | 2003/0089212 A1 | 5/2003 | Parks et al. |
| 2002/0020263 A1 | 2/2002 | Gass et al. | 2003/0090224 A1 | 5/2003 | Gass et al. |
| 2002/0020265 A1 | 2/2002 | Gass et al. | 2003/0101857 A1 | 6/2003 | Chuang |
| 2002/0020271 A1 | 2/2002 | Gass et al. | 2003/0109798 A1 | 6/2003 | Kermani |
| 2002/0056348 A1 | 5/2002 | Gass et al. | 2003/0131703 A1 | 7/2003 | Gass et al. |
| 2002/0056349 A1 | 5/2002 | Gass et al. | 2003/0140749 A1 | 7/2003 | Gass et al. |
| 2002/0056350 A1 | 5/2002 | Gass et al. | 2004/0040426 A1 | 3/2004 | Gass et al. |
| 2002/0059853 A1 | 5/2002 | Gass et al. | 2005/0215941 A1 * | 9/2005 | Bernard et al. ................ 604/20 |
| 2002/0059854 A1 | 5/2002 | Gass et al. | | | |
| 2002/0059855 A1 | 5/2002 | Gass et al. | | | |
| 2002/0059938 A1 * | 5/2002 | Fogarty et al. ............. 128/899 | * cited by examiner | | |

NEEDLELESS HYPODERMIC JET INJECTOR APPARATUS AND METHOD

BACKGROUND OF THE INVENTION

The present invention relates generally to a multiple-use needle-free (or needle-less) hypodermic jet injection devices, and to methods of reliably delivering the drug through the skin. More particularly, this present invention relates to such a device and to such method which provide an indication that the skin was sufficiently pierced by the jet to ensure that the drug was delivered. The indication is provided through measurement of the impedance.

Needle-less or needle-free hypodermic jet injection devices have been in commercial use for over 30 years. Various needleless hypodermic injection devices have been known and used in the past. These devices, also known as jet injectors, typically use highly accelerated jet of liquid moving sufficiently fast to pierce through the skin and enter the underlying tissues. The advantages of needleless devices are: generally less painful experience for patients, absence of needle-pricks, decreased probability of introducing infection, high throughput when delivering vaccinations.

The related technology includes a number of teachings, including:

U.S. Pat. No. 4,596,556, issued Jun. 24, 1986 to J. Thomas Morrow, et al.;

U.S. Pat. No. 4,913,699; issued Apr. 3, 1990 to James S. Parsons;

U.S. Pat. No. 5,730,723, issued Mar. 24, 1998, to Thomas P. Castellano, et al.;

U.S. Pat. No. 6,585,685, issued Jul. 1, 2003 to John Lawrence Staylor, et al.; and U.S. Pat. No. 6,689,093, issued Feb. 10, 2004, to Sergio Landau. WIPO publication WO 97/37705 also discloses a disposable needle-less hypodermic jet injector.

Each of these devices has limitations, deficiencies, or disadvantages, as will be apparent in view of the following detailed description of the present invention. One of the problems of these devices is that the characteristics of needleless or jet injections typically vary with the pressures exerted by the injection device, and the nozzle diameter. The main problem of these devices is related to the significant variability of patient's size, age, sex, and weight, the nature of the injection site, and the viscosity of the injectant. Especially the patient factors variability is critical as epidermis properties vary widely across the population and are affected by gender, age, race, weight, body fat, skin conditions, and other variables. The unresolved problem of prior art is overcoming this inherent variability and guaranteeing that the outer layer of skin, stratum corneum, was sufficiently pierced and the drug was delivered through that layer. Since there is no confirmation that the skin was sufficiently pierced, very high pressure jets are typically selected, which results in more painful drug delivery and unnecessary deep penetration for person with thinner skin. Still there is no absolute certainty that the drug was delivered, putting patient's treatment at risk.

Thus there is a need in improving the control of needleless drug delivery and ensuring that the stratum corneum was sufficiently pierced during application of needleless drug delivery device.

BRIEF SUMMARY OF THE INVENTION

In view of the above, it is an object of this invention to provide a method to control the piercing of the stratum corneum and delivery of the drug or vaccine through the skin during jet injection of the drug or vaccine. If the injection was not successful, the parameters of the jet can be adjusted, and the drug delivery can be repeated.

Further, it is an object of this invention to provide a needle-free jet injection device which provides for monitoring of the skin piercing during the drug delivery, thus ensuring less painful experience for the patient, as the parameters of the jet can be adjusted so as to operate at the necessary jet speeds to secure piercing of the skin. This will reduce patients discomfort and provide more control of the drug delivery process to the health professional and thus enable to avoid limitations, deficiencies, or disadvantages of the conventional technology.

In the present invention, the impedance between patient's body and the drug delivery device is measured through the liquid jet during the drug delivery process. The liquid jet completes the electrical circuit formed by impedance monitor, drug delivery device, and the patient's body. When the jet pierces stratum corneum, the impedance in the circuit immediately decreases, thus an indicating the successful drug delivery. The impedance monitor then provides a signal, visible, audible, or electronic, indicating that the process of the drug delivery through skin was successful.

Additional objects and advantages of this invention will appear from a reading of the following detailed description of exemplary preferred embodiment of the invention, taken in conjunction with the appended drawing Figures.

DETAILED DESCRIPTION OF THE INVENTION

Figure 1:
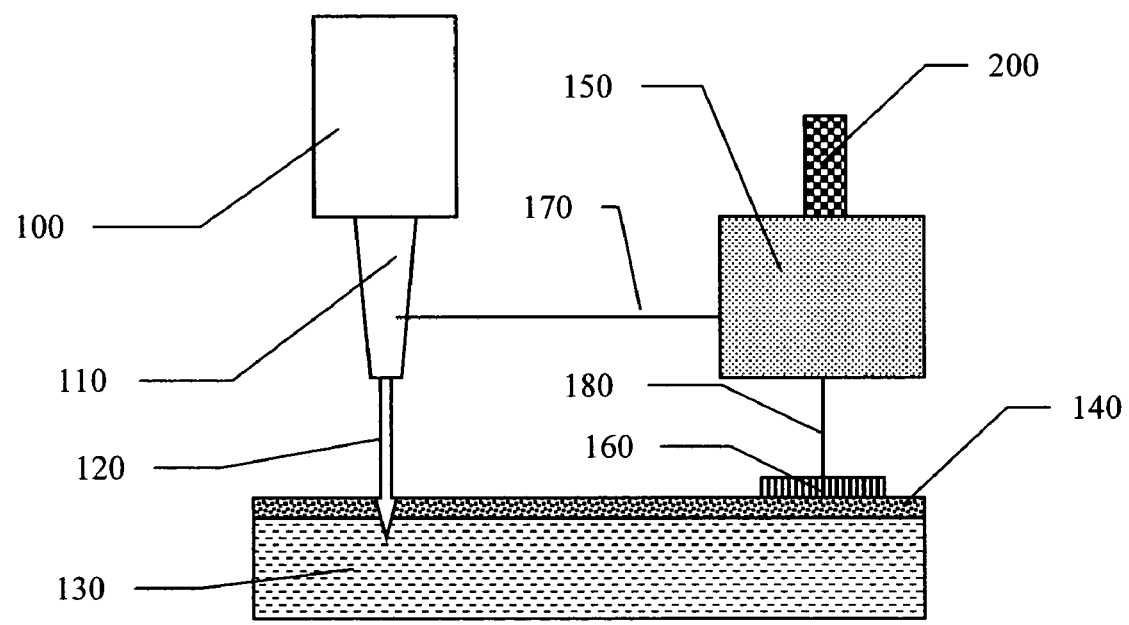
FIG. 1 shows the preferred embodiment of the invention. A jet drug delivery device 100 with a nozzle 110, said nozzle forms and directs the liquid jet 120 onto a patient's body 130. The outer layer of skin, stratum corneum 140, is penetrated by the liquid jet 120. An impedance monitor 150 is connected to the patient's body through electric wire 180 via connection pad 160, situated on the patient's body. The impedance monitor 150 is also connected through electric wire 170 to the nozzle 110. A signal generator 200, is providing audible, visible, or electronic signal indicating successful or unsuccessful piercing of stratum corneum.
Figure 2:
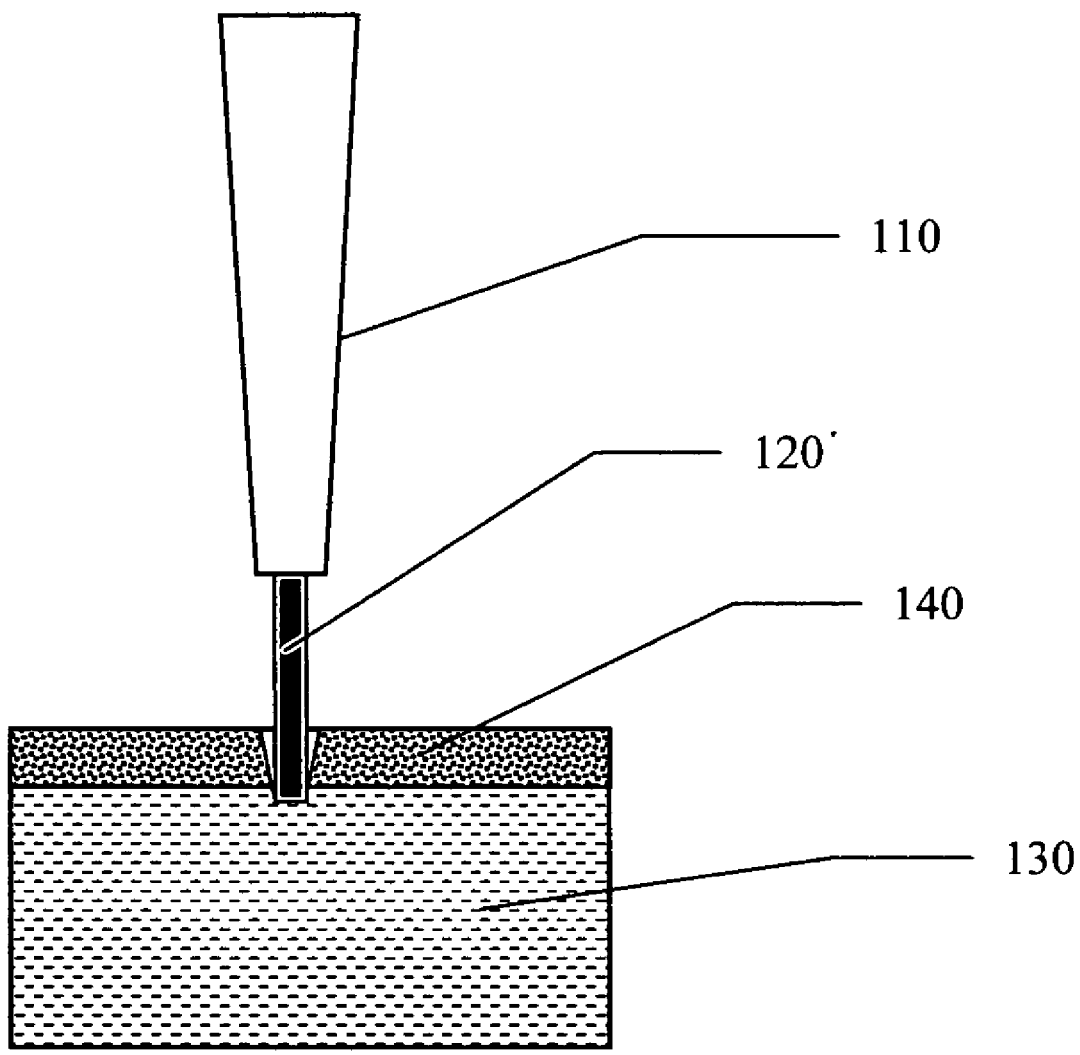
FIG. 2 shows the liquid jet 120 penetrating the outer layer of skin, stratum corneum 140. This successful penetration will result in decrease in impedance and thus signal a successful drug delivery.
Figure 3:
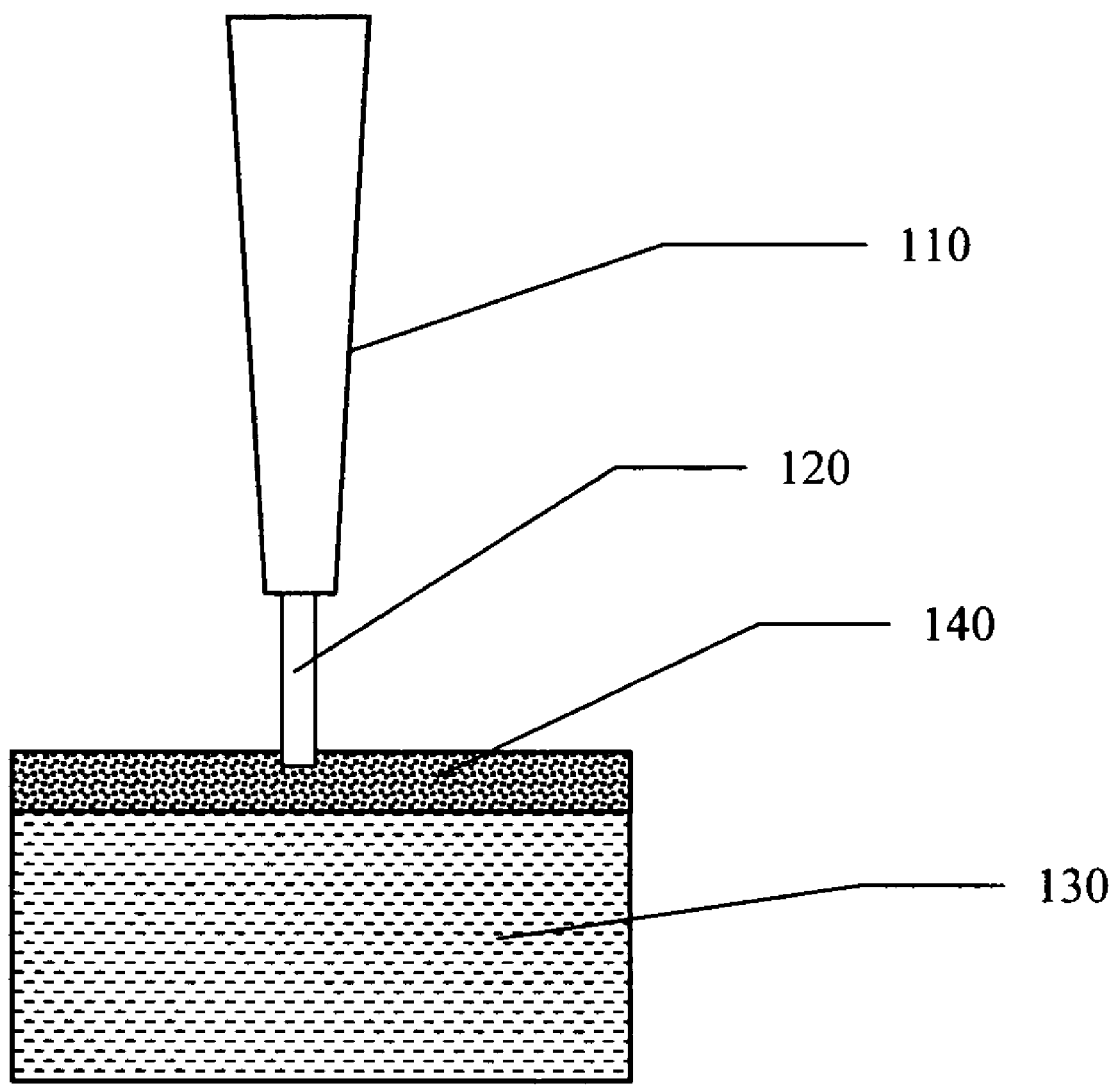
FIG. 3 shows the liquid jet 120 which fails to penetrate the outer layer of skin, stratum corneum 140. This unsuccessful penetration will not result in decreased impedance and thus signal a non-successful drug delivery.

Referring to FIG. 1, the electric circuit is formed between impedance monitor 150, patient's body, and liquid jet drug delivery device. Prior to the activation of liquid jet, the circuit is open and the impedance is very high, corresponding to open circuit impedance. The closing of the circuit is achieved by activating the liquid jet. Once the jet touched the patient's body, the circuit is closed and electric current can pass from the impedance monitor 150 into the drug delivery device nozzle 110 via wire 170, then into the liquid jet 120, then into patient's body 130, then into the connection pad 160, then back into the impedance monitor via wire 180. Thus during the liquid jet drug delivery, the electric circuit is established and enabled to measure impedance.

Once the liquid jet touched the patient's body, the impedance is principally determined by patient's skin, particularly stratum corneum, which has highest electric resistance in the circuit.

If the jet fails to penetrate the stratum corneum, the impedance monitor will measure relatively high impedance and will provide feedback indicating that the drug delivery was unsuccessful.

By dynamically monitoring the impedance through the liquid jet, the depth of the penetration of the liquid jet can be estimated based on the different impedance properties of the tissue as one penetrates deeper into the body.

The impedance monitoring or measuring devices are well known in the art. Such devices can be further connected to a computer for dynamic analysis of the impedance during the jet injection and for providing corresponding signal, which is preferably audible or optical signal, or signal in the form of computer output.

Many possible variations of the method and apparatus within the defined parameters of the present invention are apparent to those skilled in the art, without further explanation, and those variants are intended to be included within the broad scope of the invention.

What is claimed is:

1. A method of hypodermically delivering a drug into a patient's body through a patient's skin, said method comprising:
    providing a jet injection device capable of delivering the drug into the patient's body through the skin as a jet of liquid,
    forming an open electrical circuit between the patient's body and said jet injection device,
    providing an electric impedance monitor connected to said electrical circuit,
    starting measuring the electrical impedance between the patient's body and said jet injection device,
    delivering the drug into the patient's body through the skin as a jet of liquid,
    closing said electrical circuit through said jet of liquid, and
    detecting a change in the electrical impedance during the delivery of the drug into the patient's body, said change indicating a success or a failure of a piercing of the skin by the jet of liquid,
    wherein the electric impedance is measured directly through the jet of liquid.

2. The method according to claim 1, further comprising the step of generating a signal indicating the change in said electric circuit impedance when said jet of liquid penetrates the patient's skin.

3. The method according to claim 2, wherein said signal is audible.

4. The method according to claim 2, wherein said signal is visual.

5. The method according to claim 2, wherein said signal is both audible and visual.

6. A method of hypodermically injecting a drug into a patient's body and monitoring the injection success, comprising the steps of:
    providing a means for hypodermic jet injection of a drug,
    providing a means for monitoring an electric impedance between said means for hypodermic jet injection of the drug and the patient's body,
    forming an open electrical circuit between the patient's body and said means for hypodermic jet injection of a drug,
    delivering the drug utilizing said means for hypodermic jet injection of the drug into the patient's body as a jet of liquid,
    measuring the electric impedance between said means for hypodermic jet injection of the drug and the patient's body using said means for monitoring electric impedance,
    detecting changes in the electric impedance, said chances indicating a success or a failure of a penetration of the patient's body by the jet of liquid,
    generating a signal indicating the changes in the electric impedance, wherein the electric impedance is measured directly through the jet of liquid.

7. The method according to claim 6, wherein said signal is audible.

8. The method according to claim 6, wherein said signal is visual.

9. The method according to claim 6, wherein said signal is both audible and visual.

* * * * *